US00PP24698P3

(12) United States Plant Patent
Shefelbine

(10) Patent No.: US PP24,698 P3
(45) Date of Patent: Jul. 29, 2014

(54) APPLE TREE NAMED 'DS 41'

(50) Latin Name: ***Malus domestica* Borkh**
Varietal Denomination: DS 41

(76) Inventor: Doug Shefelbine, Holman, WI (US)

( * ) Notice: Subject to any disclaimer, the term of this patent is extended or adjusted under 35 U.S.C. 154(b) by 127 days.

(21) Appl. No.: 13/506,991

(22) Filed: May 30, 2012

(65) Prior Publication Data

US 2013/0326769 P1 Dec. 5, 2013

(51) Int. Cl.
*A01H 5/00* (2006.01)

(52) U.S. Cl.
USPC ..... Plt./161

(58) Field of Classification Search
CPC ..... A01H 5/0875
USPC ..... Plt./161, 172, 175
See application file for complete search history.

(56) References Cited

U.S. PATENT DOCUMENTS

PP23,649 P3 * 6/2013 Shefelbine ..... Plt./161
PP23,933 P3 * 10/2013 Shefelbine ..... Plt./161

* cited by examiner

*Primary Examiner* — June Hwu
(74) *Attorney, Agent, or Firm* — Paine Hamblen, LLP

(57) ABSTRACT

A new and distinct variety of apple tree is described, and which is characterized as to novelty by producing an attractively colored apple which is mature for harvesting and shipment on approximately October 2 under the ecological conditions prevailing in Central Washington state.

4 Drawing Sheets

Latin name: *Malus domestica* Borkh.
Varietal denomination: 'DS 41'.

BACKGROUND OF THE NEW VARIETY

The present invention relates to a new and distinct variety of apple tree '*Malus domestica* Borkh' and which has been denominated varietally hereinafter as 'DS 41', and more particularly to an apple tree which bears an attractive highly colored fruit which is distinguished as to novelty by its improved fruit pressure, brix, pH and harvesting date 22 days later as compared to the closest known variety, and when the present variety is grown under the ecological conditions prevailing near Grant County, Wash. in the central region of Washington State.

ORIGIN AND ASEXUAL REPRODUCTION

It has long been recognized that an important factor contributing to the success of any new variety of apple tree bearing fruit for the fresh market is its ability to be stored and then shipped to various local and long distance markets. Similarly, other significant factors affecting the commercial viability of any new strain of apple relates to the fruit flavor as reflected by its acidity as well as its sugar content.

The new variety 'DS 41' is noteworthy in producing a fruit which is ripe for harvesting and shipment at approximately Oct. 2, 2011 under the ecological conditions prevailing near Grant County, Wash. Further, in contrast to the apple tree that is most closely similar to the new variety, that being, the 'Honeycrisp' apple tree (U.S. Plant Pat. No. 7,197), which normally harvests about September 10 under the ecological conditions prevailing in Grant County, Wash. The present new and novel apple tree is distinguished therefrom by producing a fruit which is harvested 22 days later as compared to the 'Honeycrisp' apple tree when grown in the same geographical location, but which exhibits a fuller and more intense streaked coloration, and which further has sunken lenticels giving it a slightly different (hammered) appearance. The fresh quality is further unique in that it is very crisp and juicy, and these same characteristics are maintained at nearly the same levels following the storage of the fruit for prolonged periods and up to four months at common storage temperatures.

As a general matter, the new variety of apple tree produces a sub-acid apple that has greater fruit pressure, a lower pH and higher titratable acid, and a slightly lower sugar content when compared to the fruit produced by the 'Honeycrisp' apple tree (U.S. Plant Pat. No. 7,197) when sampled at same harvesting date, and also following four months in common storage.

The new variety of apple tree as described herein, was discovered by me within the cultivated region of my apple orchard, and which is located at N6485 Shefelbine Rd., La Cross County, Wis. In this regard, seeds from an open pollinated 'Honeycrisp' apple tree (U.S. Plant Pat. No. 7,197) were collected in 1990 and then planted in 1991 at the aforementioned orchard. This orchard is located in USDA Hardiness Zone 4A. After a suitable growing period, the new variety 'DS 41' was selected from the surviving seedlings during the 2002 growing season. 'DS 41' originated as a single plant. Thereafter, second generation trees were budded onto M26 rootstock (unpatented) in August 2007, and then planted in a commercial nursery block which was located in Grant County, Wash. in the Spring of 2009. The aforementioned Grant County nursery block is located in USDA Hardiness Zone 6b. The budding wood employed to produce the aforementioned trees was derived from the original 'DS 41' plant. The fruit produced by these second generation asexually produced trees were observed during the 2010 and 2011 growing seasons. The tree and fruit produced by these second generation trees were found to be identical to the trees and fruit produced by the original identified chance seedling during the 2002 growing season. Additionally, the blossoms, buds, leaves and bark as described hereinafter was identical to that as seen in the originally discovered plant which was growing on its own roots.

Figure 1:
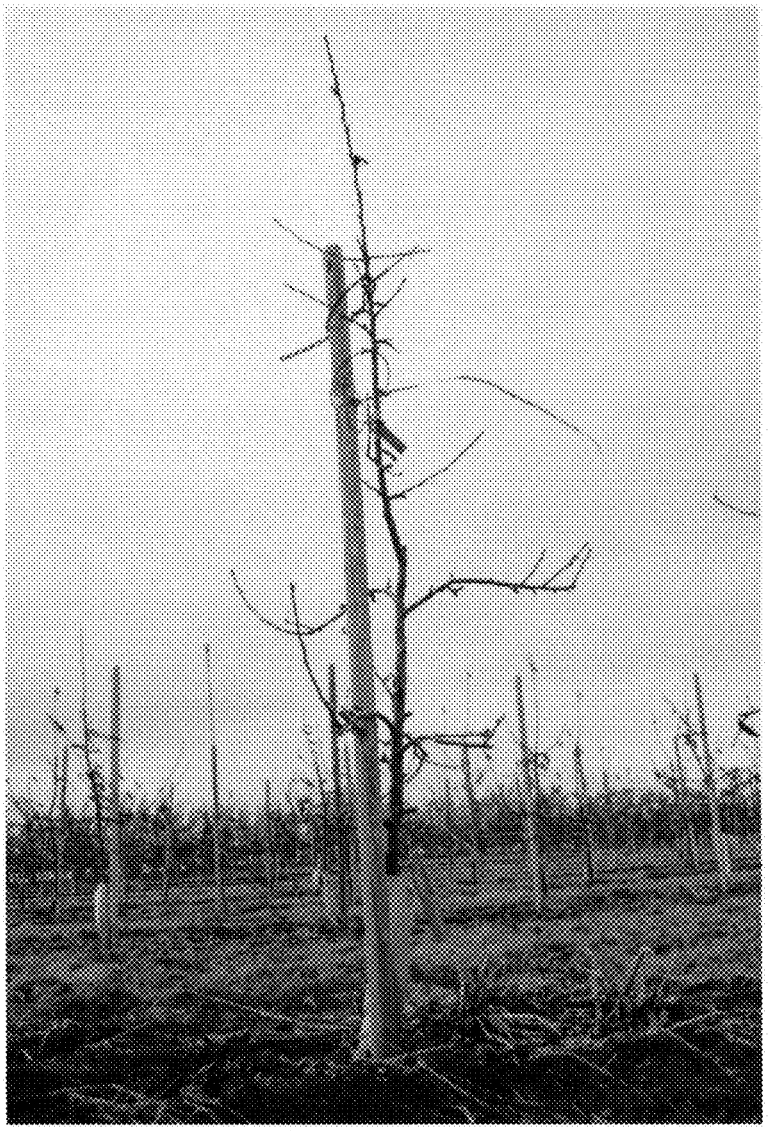
FIG. 1 is a photograph of the present variety of apple tree growing under typical ecological conditions in the aforementioned nursery orchard which is located in central Washington state.
Figure 2:
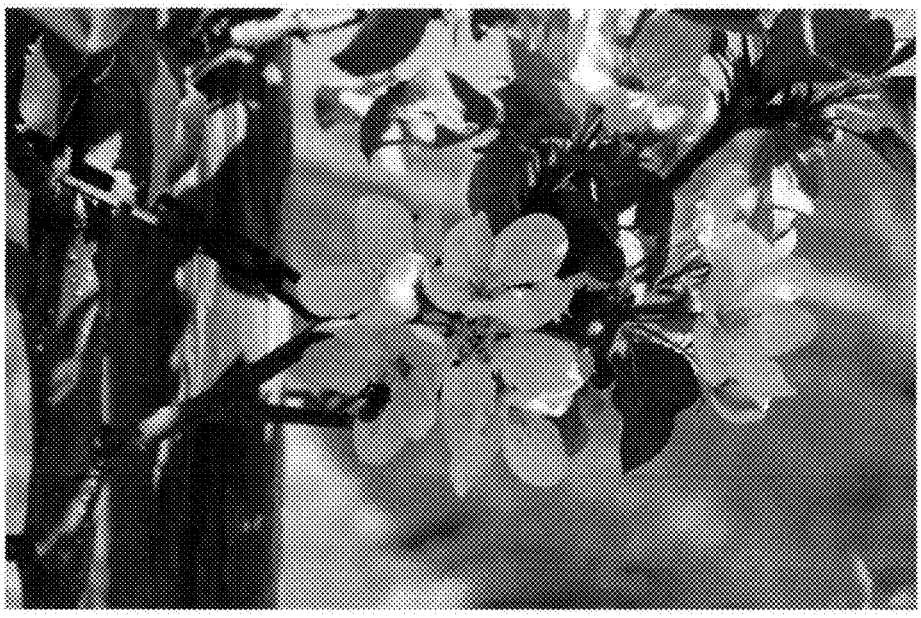
FIG. 2 is a photograph of a fruiting branch of the present new variety of apple tree at full bloom.
Figure 3:
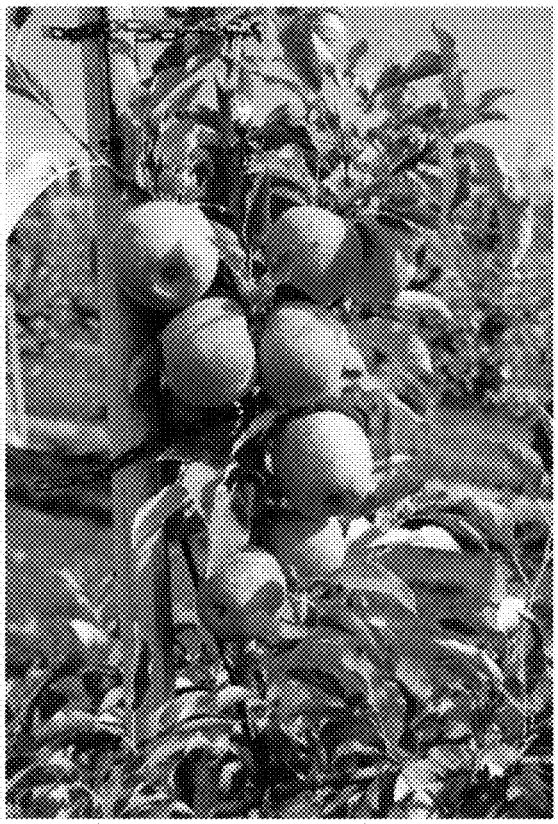
FIG. 3 is a photograph of a mature fruiting branch, at full harvest maturity, of the present variety.
Figure 4:
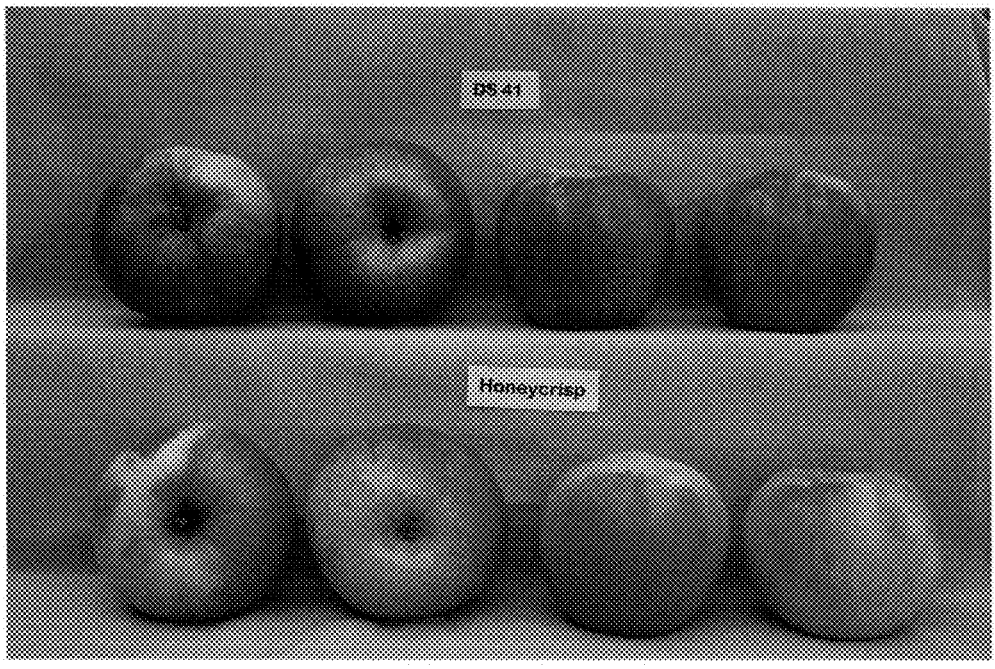
FIG. 4 is a photograph which compares the fruit of the present variety against the fruit produced by a 'Honeycrisp' apple tree (U.S. Plant Pat. No. 7,197) when grown under similar environmental conditions.

The colors in the enclosed photographs are as nearly true as is reasonably possible in color photographs of this type. However, due to chemical development, processing and printing, the leaves and fruit depicted in these photographs may or may not be accurate when compared to the actual botanical specimens. For this reason, future color references should be made to the color plates (Royal Horticultural Society of Great Britain) and other common color descriptions as provided hereinafter. Occasionally, common names will also be used.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Tree

*Size.*—Generally — The tree as discussed, hereinafter, is a second generation tree which is three years old, and which is described as it would be seen while growing at the earlier mentioned orchard which is located in Grant County, Wash. All color references are from The R.H.S. Colour Chart provided by The Royal Horticultural Society of Great Britain.

*Type.*—The present variety of tree is trained and growing on a central leader arrangement. As trained, the variety is considered precocious.

*Spur development.*—Generally — Moderately heavy numbers of spurs are produced.

*Vigor.*—Considered moderate for the species.

*Shape.*—Generally — Considered upright to upright spreading. However, to some degree, the training of the tree on a central leader type arrangement will dictate the overall shape of the tree.

*Tree height.*—At three years, about 6.5 feet.

*Crown diameter.*—At three years, about 4.0 feet.

*Hardiness.*—The present variety is considered hardy for the region it is being grown in, that is, USDA Zone 6a.

*Fruit productivity.*—Considered moderately high for the species.

Trunk

*Size.*—About 3.3 cm. in diameter when the trunk is measured at a height of about 20 cm. about the graft union.

*Bark texture.*—Generally — Considered smooth for a tree of only three years old.

*Bark color.*—Grey-brown (RHS 199C).

*Lenticels.*—Numbers — Present, and moderate in number, and averaging about 10 lenticels per 4 square cm. area.

*Lenticels.*—Shape — Variable, oval to elongated and oriented substantially horizontally.

*Lenticels.*—Width — 0.9 to about 1.7 mm.

*Lenticels.*—Length — 3.2 to about 6.6. mm.

*Lenticels.*—Color — Grey-yellow (RHS 161B).

Branches

First year branches:

*Diameter.*—About 4.2 to about 5.1 mm. in diameter.

*Length.*—About 20.9 to about 32.3 cm.

*Bark color.*—Generally — Grey-purple (RHS 183A).

*Lenticels.*—Numbers — About 9 lenticels appear per running cm. of branch length.

*Lenticels.*—Shape — Elongated and oriented substantially vertically.

*Lenticels.*—Length — About 0.7 to about 1.1 mm.

*Lenticels.*—Width — About 0.3 to about 0.5 mm.

*Lenticels.*—Color — Yellow-white (RHS 158A).

*Branch pubescence.*—Generally — Present, however it is generally light in abundance.

*Internodes spacing.*—About 27.1 to about 40.1 mm. between the internodes.

Two year old branches:

*Diameter.*—About 7.5 to about 8.8 mm.

*Spur development.*—Considered moderate to moderately heavy.

*Spur length.*—About 7.5 to about 46.1 mm.

*Bud diameter.*—About 6.0 to about 9.2 mm.

*Bud color.*—Grey-purple (RHS 187A).

*Lenticels.*—Numbers — Numerous and averaging about 7 lenticels per square cm.

*Lenticels.*—Shape — Round.

*Lenticels.*—Diameter — About 1-2 mm.

*Lenticels.*—Color — Yellow-white (RHS 158A).

Scaffold branches:

*Size.*—Variable, and ranging in size from about 10 to about 16.3 mm. in diameter when measured at a distance of about 5 cm. from the trunk.

*Crotch angle.*—Generally — As trained, this measurement is moderately flat to flat, that is, about 85 to about 90 degrees from the vertical.

*Branch color.*—Generally — Grey-brown (RHS N199C).

*Lenticels.*—Numbers — Considered few in number. Typically 2 lenticels per square cm. are found.

*Lenticels.*—Shape — Typically oval.

*Lenticels.*—Length — About 1.8 to about 2.6 mm.

*Lenticels.*—Width — About 1.1 to about 1.3 mm.

*Lenticel orientation.*—Generally — Horizontal.

*Lenticel color.*—Orange-white (RHS 159A).

Leaves

*Shape.*—Generally — Considered broadly acute, and upwardly folding.
*Texture.*—Dorsal surface — Smooth and leathery and having sunken veins.
*Texture.*—Ventral surface — Smooth, and having protruding veins.
*Sheen.*—The dorsal surface has a high sheen.
*Pubescence.*—On the ventral surface, the pubescence covers nearly the entire surface and is considered moderately dense.
*Pubescence color.*—Green-white (RHS 157B).
*Length.*—About 82.7 to about 111.4 mm.
*Width.*—About 56.6 to about 69.2 mm.
*Marginal form.*—Generally — Considered serrate, and occasionally bi-serrate regions may be found.
*Tip shape.*—Acuminate.
*Base.*—Rounded.
*Stipules.*—Generally — Present on most petioles.
*Stipules.*—Numbers — Typically 1 to 2 are present.
*Shape.*—Acicular and further curving towards the petiole.
*Stipule length.*—About 9.6 mm.
*Stipule width.*—About 1.9 mm.
*Stipule color.*—Both the dorsal and ventral surfaces are considered green (RHS 138B).
*Stipule pubescence.*—None is evident.
*Leaf blade color.*—Dorsal surface — Green (RHS 137A).
*Leaf blade color.*—Ventral surface — Yellow-green (RHS 146B).
*Mid-vein shape.*—Prominent and having a considerable amount of fine pubescence on the lower surface of the vein.
*Mid-vein width.*—About 1.1 mm. to about 1.6 mm.
*Mid-vein upper surface color.*—Yellow-green (RHS 145D).
*Mid-vein lower surface color.*—Yellow-green (RHS 146B).
*Mid-vein pubescence.*—Generally speaking, the entire ventral surface is covered with a moderately dense pubescence which has a color that is green-white (RHS 157B).
*Leaf petiole.*—Length — About 29.1 to about 47.6 mm.
*Leaf petiole.*—Shape — A shallow groove runs the entire length of the dorsal surface.
*Leaf petiole.*—Diameter — About 1.8 to about 2 mm.
*Leaf petiole.*—Color — The dorsal surface has a grey-purple color (RHS 186C). The ventral surface has a yellow-green color (RHS 194C). Occasionally, a light highlight is found at the basal end and on the ventral surface, and which is grey-purple (RHS 185A).
*Petiole pubescence.*—Generally, considered abundant and moderately dense, and located over the entire length, and circumference of the petiole.
*Petiole pubescence.*—Color — Green-white (RHS 157B).

Flower

*Date of full bloom.*—About May 9, 2011 under the ecological conditions prevailing near Grant County, Wash. First bloom was noted on May 6. The bloom was completed on May 14.
*Number of blossoms per bud.*—5-6 blossoms may be found.
*Flower size.*—Generally speaking, it is considered to be a medium-large flower for the species. When fully expanded, the diameter of the flowers range from about 49.8 to 57.2 mm. The flower fragrance is mildly apple-like.
*Petals.*—Numbers — 5.
*Petals.*—Width — About 18.3 mm.
*Petals.*—Length — About 24.5 mm.
*Petals.*—Color — Both the upper and lower surface of the petal are white (RHS N155D). The ventral surface has highlights which are red-purple, in color (RHS 64B).
*Petal shape.*—Elliptic.
*Stamen.*—Numbers — About 19-20.
*Filament.*—Length — About 4.2 to about 12.1 mm.
*Filament.*—Color — White (RHS 155C).
*Anthers.*—Shape — Elongated and heart shaped.
*Anthers.*—Dimensions — About 1 mm. wide and about 1.4 mm. long.
*Anthers.*—Mature Color — Yellow (RHS 10D). Pollen: Generally moderate in abundance and yellow in color (RHS 10D).
*Pistil.*—Length — About 11.7 to about 14.4 mm.
*Styles.*—Numbers — About 5.
*Styles.*—Form — The styles are fused together at about ⅓ the distance from the base.
*Styles.*—Color — Yellow-green (RHS 145B).
*Stigma.*—Shape — Round and club shaped.
*Stigma.*—Diameter — About 0.5 mm.
*Stigma.*—Color — Yellow-green (RHS 153B).
*Sepals.*—Numbers — Typically 5 per blossom.
*Sepals.*—Shape — Considered thin, and deltoid shaped, and curved back over the peduncle.
*Sepals.*—Tip Shape — Generally acuminate.
*Sepals.*—Base shape — truncate.
*Sepals.*—Length — About 11.1 mm.
*Sepals.*—Width — About 4.1. mm.
*Sepals.*—Pubescence — Moderate, and white in color.
*Sepal color.*—Dorsal surface — Yellow-green (RHS 146C).
*Sepal color.*—Ventral surface — Yellow-green (RHS 148D).
*Sepal tip color.*—Red-purple (RHS 64B).
*Peduncle.*—Length — About 20.5 to about 24.3 mm.
*Peduncle.*—Color — Yellow-green (RHS 146B). Occasionally, the basal end of the peduncle may have highlights of a red-purple color (RHS 64B).
*Peduncle.*—Surface texture — A white downiness is present over the entire surface. The color of this downiness is not distinctive of the variety.

Fruit

*Form.*—Generally — The present variety produces fruit which are considered irregularly round and conical in shape, and the fruit exhibits an overall lopsided appearance. The present fruit is not considered crowned and does not exhibit any ribbing.
*Size.*—Considered medium large for the species at normal crop loading levels.
*Diameter.*—About 74.4 mm when measured in the axial diameter. The present variety also has an average diameter of 84.7 mm. when measured in the equatorial plane.
*Stem.*—Length — Considered stout. The length of the fruit stem is about 9.2 to about 22.9 mm.
*Stem.*—Diameter — About 3.5 mm.
*Stem cavity.*—Width — About 27.2 to about 36 mm.
*Stem cavity.*—Depth — About 14.2 to about 20.8 mm.
*Stem cavity.*—Shape — Obtuse. No stem cavity lipping is evident.

*Stem bowl.*—Russet — Very little russet is detected, and when found, is typically located only at the base.
*Basin cavity.*—Width — About 28.9 to about 35.6 mm.
*Basin cavity.*—Depth — About 9.2 to about 14.4 mm.
*Basin cavity.*—Shape — Overall the cavity is considered wide and sloping.
*Eye.*—Shape — Erect in form, and occasionally having reflexed tips.
*Sepal color.*—Yellow-green (RHS 146D).
*Sepals.*—Surface texture — Considered moderately downy.
*Sepals.*—Downy color — Green-white (RHS 157D).
*Skin.*—Surface texture — Considered smooth and having shallow lenticel dimpling which gives it a "hammered" look.
*Skin bloom.*—Present and considered moderate in amount.
*Skin texture.*—Considered brittle.
*Skin thickness.*—Considered average for the species.
*Skin appearance.*—Streaked.
*Skin under color.*—Yellow-green (RHS 151D).
*Streak over color.*—Red (RHS 53A).
*Streak under color.*—Red (RHS 46B). As a general matter, 80 to about 95% of the surface is colored.
*Skin lenticels.*—Numbers — Numerous and uniform in their distribution. Typically, 8 per square cm. are found.
*Skin lenticels.*—Shape — Round and quite conspicuous in the streaked areas.
*Skin lenticels.*—Diameter — About 0.7 to about 1 mm.
*Skin lenticels.*—Color — White (RHS 155B).
*Core position.*—Generally speaking, it is considered median.
*Core line position.*—Basal meeting.
*Core diameter.*—About 39.2 mm.
*Core length.*—About 31.8 mm.
*Core shape.*—Generally considered flat and conical.
*Cell number per fruit.*—5.
*Cell shape.*—Considered elliptical.
*Cell length.*—About 17.2 mm.
*Cell depth.*—About 5.3 mm.
*Stamen position.*—Generally, basal.
*Axis.*—Generally, axial and closed.
*Seed numbers.*—Typically 2. Occasionally 1.
*Seed shape.*—Acute.
*Seed length.*—About 8.1 to about 9.1 mm.
*Seed width.*—About 4.8 to about 5.7 mm.
*Seed color.*—Brown (RHS 200C).
*Flesh texture.*—Fine, crisp, and melting. The flesh is sub-acid and juicy.
*Flesh color.*—Yellow (RHS 11D). The flesh of the present fruit will brown slightly following exposure to the atmosphere upon the cutting of the fruit.
*Flesh aroma.*—Apple-like and moderate in intensity.
*Date of harvest.*—Oct. 2, 2011 under the ecological conditions prevailing in Grant County, Wash. The present variety is a single pick variety.
*Fruit pressure.*—The apple tree of the present variety produces fruit at harvesting which has a fruit pressure of about 16.4 pounds. In relative comparison to the fruit produced by the 'Honeycrisp' apple tree (U.S. Plant Pat. No. 7,197), the fruit pressure of the present variety is higher. The 'Honeycrisp' apple tree produces fruit at the same geographical location which has a fruit pressure of about 15.1 pounds. Once the fruit is subjected to storage conditions, the fruit produced by the present variety of apple tree had a fruit pressure on Jan. 23, 2012 of 15.9 pounds as compared to the fruit of the 'Honeycrisp' apple tree which had a fruit pressure of about 13.5 pounds.
*Brix.*—Upon harvesting, the fruit produced by the present variety of apple tree had a brix of about 13.5 as compared to the brix of 14.3 for the fruit produced by the 'Honeycrisp' apple tree (U.S. Plant Pat. No. 7,197) when grown under similar environmental conditions. When measured on Jan. 23, 2012, the new variety had a brix of about 13.9 as compared to the fruit of the 'Honeycrisp' apple tree which had a brix of about 14.2.
*pH.*—Upon harvesting on Oct. 2, 2011, the fruit of the present new variety of apple tree had a pH of about 3.43 as compared to a pH of about 3.75 for the fruit produced by the 'Honeycrisp' apple tree when grown under similar conditions. When measured on Jan. 23, 2012, the pH of the fruit produced by the present variety was about 3.52 as opposed to the pH of the 'Honeycrisp' apples stored under identical storage conditions which had a pH of about 3.75.
*Titratable acid.*—Upon harvest, the fruit produced by the present variety of apple tree had a titratable acid concentration of 0.82 grams per 100 ml. as compared to the titratable acid found in the fruit produced by the 'Honeycrisp' apple tree, when grown under similar conditions of about 0.52 grams per 100 ml. When measured on Jan. 23, 2012, the fruit of the new variety of apple tree had a titratable acid concentration of 0.62 grams per 100 ml. as opposed to the 'Honeycrisp' apple tree, when stored under identical conditions, of about 0.45 grams per 100 ml.
*Keeping quality.*—Considered excellent. The present variety has been kept up to 5 months in cold storage with no substantial deleterious effects noted.
*Pollination.*—Generally — Any diploid apple maturing in approximately the same blooming season will be suitable.
*Fruit use.*—Fresh dessert apple.
*Disease and insect resistance.*—The present variety is considered to be susceptible to all insects and diseases found in the region of Central Washington state.

Although the new variety of apple tree herein denominated varietally as 'DS 41' possesses the characteristics recited above when grown under the ecological conditions prevailing in Grant County, Wash., it should be understood that the variations of the usual magnitude and characteristics incident to changes in growing conditions, fertilization, pruning and pest control will be expected.

Having thus described and illustrated my new variety of apple tree, what I claim is new, and desire to secure by Plant Letters Patent is:

1. A new and distinct variety of apple tree as substantially illustrated and described, and which is characterized as to novelty by producing an attractively colored apple which is mature for harvesting and shipment on approximately October 2 under the ecological conditions prevailing near Grant County, Wash.

* * * * *